(12) United States Patent
Chung et al.

(10) Patent No.: US 7,655,417 B2
(45) Date of Patent: Feb. 2, 2010

(54) VCAM-1 SPECIFIC MONOCLONAL ANTIBODY

(75) Inventors: Junho Chung, Pohang (KR); Ji Eun Lee, Koyang (KR); Eun Kyung Ryu, Seoul (KR); Sukmook Lee, Seoul (KR)

(73) Assignee: Hanwha Chemical Corporation, Seoul (KR)

( * ) Notice: Subject to any disclaimer, the term of this patent is extended or adjusted under 35 U.S.C. 154(b) by 47 days.

(21) Appl. No.: 11/756,437

(22) Filed: May 31, 2007

(65) Prior Publication Data

US 2007/0280941 A1    Dec. 6, 2007

(51) Int. Cl.
  G01N 33/53    (2006.01)
  C12N 15/87    (2006.01)
  C12P 21/06    (2006.01)
  C07K 16/00    (2006.01)
  C07K 16/28    (2006.01)

(52) U.S. Cl. ............... 435/7.1; 530/387.3; 530/388.22; 530/388.7; 435/69.1; 435/455

(58) Field of Classification Search ................ None
  See application file for complete search history.

(56) References Cited

U.S. PATENT DOCUMENTS 5,766,910 A * 6/1998 Fukuda et al. ............. 435/193
6,632,927 B2 * 10/2003 Adair et al. ............... 530/387.3

FOREIGN PATENT DOCUMENTS

WO    WO 93/14220    * 7/1993

OTHER PUBLICATIONS

Rudikoff et al Single amino acid substitution altering antigen-binding specificity. Proc Natl Acad Sci U S A. Mar. 1982;79(6):1979-83.*
Panka et al. Variable region framework differences result in decreased or increased affinity of variant anti-digoxin antibodies. Proc Natl Acad Sci U S A. 85(9):3080-3084, 1988.*
Owens RJ, Young RJ. The genetic engineering of monoclonal antibodies. J Immunol Methods. 168(2):149-165, 1994.*
Briskin et al., Structural requirements for mucosal vascular addressin binding to its lymphocyte receptor alpha 4 beta 7. Common themes among integrin-Ig family interactions. J Immunol. Jan. 15, 1996;156(2):719-26.*
GenBank Accession No. NP_999056. vascular cell adhesion molecule [Sus scrofa]. MAM Feb. 15, 2009.*
Campbell A, General properties and applications of monoclonal antibodies, Elsevier Science Publishers, section 1.1, pp. 1-32, 1984.*

* cited by examiner

*Primary Examiner*—Maher M Haddad
(74) *Attorney, Agent, or Firm*—Joseph Hyosuk Kim; JHK Law

(57) ABSTRACT

The present invention relates to a monoclonal antibody that specifically binds to vascular cell adhesion molecule-1 (VCAM-1 or CD106). Specifically, the present invention relates to an antibody that specifically binds to both human and mouse vascular cell adhesion molecule-1 (VCAM-1), a method for producing the same, a composition for diagnosis or treatment comprising them and a method for diagnosis or treatment using them. The monoclonal antibody of the present invention is the first recombinant monoclonal antibodies that is specific to human and mouse VCAM-1. In addition, the monoclonal antibody of the present invention shows a strong affinity to VCAM-1 expressed in rat skeletal muscle and porcine endothelial cells as well as human and mouse endothelial cells and is found to strongly inhibit the interaction between leukocytes and activated endothelial cells. Accordingly, the monoclonal antibody of the present invention can inhibit a VCAM-1 mediated adhesion of leukocytes to endothelial cells and potently treat VCAM-1 mediated disease, especially inflammatory disease or cancer.

16 Claims, 5 Drawing Sheets

FIG. 2

VCAM-1 SPECIFIC MONOCLONAL ANTIBODY

BACKGROUND OF THE INVENTION

1. Field of the Invention

The present invention relates to a monoclonal antibody that specifically binds to vascular cell adhesion molecule-1 (hereinafter, referred to simply as "VCAM-1"). Specifically, the present invention relates to a monoclonal antibody that specifically binds to both human and mouse vascular cell adhesion molecule-1 (VCAM-1), a method for producing the same, a composition for diagnosis or treatment comprising them and a method for diagnosis or treatment using them. The invention also relates to a method of inhibiting VCAM-1 mediated leukocyte adhesion to endothelial cells.

2. General Background and State of the Art

Cell adhesion molecules (CAMs) are important for the recruitment of leukocytes from circulating blood to the endothelium in the inflammatory reaction. Endothelial cells as an active responder in response to extracellular stimuli express various CAMs, such as E- and P-selectins and members of the immunoglobulin superfamily including intercellular cell adhesion molecule (ICAM)-1, -2, and -3, vascular cell adhesion molecule (VCAM)-1, which interact with carbohydrate ligands and integrins expressed in leukocytes. Accordingly, because of the central roles of CAMs that mediate the accumulation of leukocytes in inflammation, blocking CAMs is thought to be a promising strategy for therapeutic intervention in inflammatory disorders.

Among CAMs, VCAM-1, CD106, is expressed in dominantly and inducibly expressed on endothelial cells upon activation by lipopolysaccharide (LPS), interleukin-1 (IL-1), interferon-γ (INFγ) or tumor necrosis factor alpha (TNFα). VCAM-1 binds to very late antigen-4 (VLA-4), α4β1 integrin, expressed on activated leukocytes in inflammation and immune rejection and plays a critical role in promoting the interaction between endothelial cells and leukocytes including monocyte and T cells. Currently, increasing attention is being paid to VCAM-1-VLA-4 interaction as targets for therapeutic interventions in inflammatory diseases. For example, small peptide antagonists of integrin α4β1, TR14035, and a α4 integrin antibody, Tysabri or Natalizumab, are effective in ameliorating pathology in inflammatory bowel disease, multiple sclerosis, and asthma. TR14035 and Natalizumab are currently in Phase II and III respectively. Additionally, according to recent increasing evidence, VCAM-1 is also closely implicated in cancer progression. In detail, first, soluble VCAM-1 is regarded as a marker of the diagnosis of various cancers. Second, VCAM-1 which is expressed in tumor periphery plays a key role in facilitating the homing of bone marrow-derived progenitor cells for tumor neovascularization. Third, VCAM-1 is important in extravasation of circulating cancer cells, a key step in metastasis. Fourth, down-regulation of VCAM-1 in a highly immune-resistant cancer cell line was found to lead to reduced tumor immune evasion. In this regards, there are increasing needs for diagnosis and therapy of anti-adhesion drugs in cancer treatment.

Despite recent attention to VCAM-1-VLA-4 interaction, the development of a neutralizing antibody to VCAM-1 has not been actively studied. Although M/K-2.7, a monoclonal antibody to mouse VCAM-1, is recently developed and shows reduced effect on joint inflammation in collagen-induced arthritis mouse model, the usefulness of the antibody should be further tested for clinical application. Until now, most clinical trials of anti-adhesion therapies have used humanized monoclonal antibodies. In this regards, the development of a monoclonal antibody specific to mouse and human VCAM-1 for preclinical and clinical study and capable of the conversion of humanized antibody is being urgently required.

In the present study, we for the first time generated a rabbit/human chimeric monoclonal antibody specific to human and mouse VCAM-1 which contains rabbit heavy chain ($V_H$) and light chain ($V_L$) variable domain and human heavy chain ($C_{H1}$) and light chain ($C_L$) constant domain from synthetic antibody library. This antibody specifically recognizes human, mouse, rat, and porcine VCAM-1 expressed in various cell types such endothelial cells and skeletal muscle cells. Furthermore, it has a strong activity of blocking the interaction between U937 human promonocytic leukocytes and activated endothelial cells. Finally, we identified the epitope regions against VCAM-1 specific antibody whose sequences are derived from mouse VCAM-1. In summary, the present application describes a potential therapeutic monoclonal antibody dual specific to human and mouse VCAM-1.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIG. 1a: 0.2 μg of anti-VCAM-1 Fab was resolved by SDS-PAGE and visualized by Coomassie Blue staining. The anti-VCAM-1 Fab with a molecular mass of 25 kDa is indicated by an arrow. FIG. 1b: Recombinant human and mouse VCAM-1/Fc chimera coated to 96 well plates were detected with preimmune, immune serum, and purified anti-VCAM-1 Fab, respectively, as described under Examples. FIG. 1C: Different amounts of recombinant human and mouse VCAM-1/Fc chimera were loaded onto a gel and subjected to immunoblotting with anti-VCAM-1 Fab as described under Examples.

FIG. 2 shows sequences of heavy-chain and light-chain variable domains of anti-VCAM-1 Fab clones. The selected Fab clones were subjected to DNA sequencing and then the identified sequences of heavy-chain ($V_H$) and light-chain ($V_L$) variable domains of anti-VCAM-1 Fab clones were depicted as indicated. FR means framework region. CDR designates complementarity-determining region. Sequences of humanized antibody derived from anti-VCAM-1 Fab clones are also depicted.

FIG. 4a: PAECs treated with 400 μM $H_2O_2$ were incubated in the absence (thin line) or presence (thick line) of anti-VCAM-1 Fab or anti-VCAM-1 IgG and then subjected to adhesion assay with CSFE-labeled U937 cells as described under Examples. The extent of the U937 binding to endothelial cells was detected using flow cytometry. PAEC culture in the absence of $H_2O_2$ (dotted line) was used for detecting basal binding of U937 to resting endothelial cells.

FIG. 4*b*: The % values of CFSE-labeled U937 bound to endothelial cells are depicted as vertical bars. The results shown represent the means±S.D. obtained from the representative of two separate experiments performed in duplicates.

DETAILED DESCRIPTION OF THE PREFERRED EMBODIMENTS

Figure 1A:
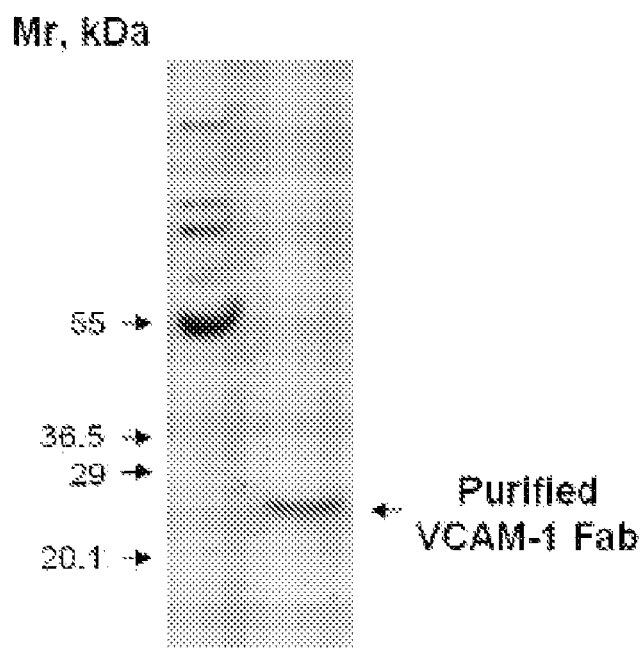
FIGS. 1a-1c show purification and characterization of an anti-VCAM-1 Fab clone specific to human and mouse VCAM-1.

In the present application, "a" and "an" are used to refer to both single and a plurality of objects.

In one embodiment of the present invention for solving the above-described problems, there is provided a monoclonal antibody that specifically binds to both human and mouse vascular cell adhesion molecule-1 (VCAM-1).

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., dispecific antibodies). The term "antibody" also includes antigen binding forms of antibodies, including fragments with antigen-binding capability (e.g., Fab', F(ab')2, Fab, Fv and rIgG). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992, J. Immunol. 148:15467), Pack and Pluckthun (1992, Biochemistry 31:1579), Hollinger et al. (1993, supra), Gruber et al. (1994, J. Immunol.: 5368), Zhu et al. (1997, Protein Sci. 6:781), Hu et al. (1996, Cancer Res. 56:3055), Adams et al. (1993, Cancer Res. 53:4026 and McCartney et al. (1995, Protein Eng. 8:301)

Also, the term "monoclonal antibody" as used herein, refers to an antibody molecule that has been obtained from a substantially identical antibody clone, which shows single-binding specificity and affinity for a specific antigen.

Typically, an immunoglobulin has a heavy and light chain. Each heavy and light chain contains a constant region and a variable region (the regions are also known as "domains"). Light chain and heavy chain variable regions contain three hypervariable regions called "complementarity-determining regions" or "CDRs" and four "framework" regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located.

In one preferred embodiment, the present invention relates to a monoclonal antibody comprising a light chain variable region that comprises light chain CDR1 as defined by SEQ ID No. 5; light chain CDR2 as defined by SEQ ID No. 6; and light chain CDR3 as defined by SEQ ID No. 7. More preferably, the monoclonal antibody of the present invention comprises a light chain of which the amino acid sequence is defined by SEQ ID No. 1.

In another preferred embodiment, the present invention relates to a monoclonal antibody comprising a heavy chain variable region that comprises heavy chain CDR1 as defined by SEQ ID No. 8; heavy chain CDR2 as defined by SEQ ID No. 9 or SEQ ID No. 11; and heavy chain CDR3 as defined by SEQ ID No. 10 or SEQ ID No. 12. More preferably, the monoclonal antibody of the present invention comprises a heavy chain of which the amino acid sequence is selected from the group consisting of the amino acid sequences that are defined by SEQ ID NOS. 2, 3 and 4.

Also, the monoclonal antibody of the present invention may comprise both the above light chain variable region and heavy chain variable region.

In the meantime, the monoclonal antibody of the present invention may be generated by grafting the above complementarity-determining regions (CDRs) of anti-VCAM-1 Fab onto framework (FR) in variable regions of known therapeutic antibody. Preferably, the FR may comprise an amino acid sequence as described in FIG. 2.

In another preferred embodiment, the monoclonal antibody of the present invention may be humanized for treating a human disease more properly. More preferably, the humanized monoclonal antibody may comprise a light chain of which the amino acid sequence is defined by SEQ ID No. 13 and/or a heavy chain of which the amino acid sequence is defined by SEQ ID NOS. 14 or 15.

A "humanized antibody" is an immunoglobulin molecule that contains minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity.

Humanization can be essentially performed following the method of Winter and co-workers (Jones et al., Nature 321: 522-525(1986); Riechmann et al., Nature 332:323-327 (1988); Verhoeyen et al., Science 239:1534-1536(1988)), by substituting CDRs of non-human species for the corresponding sequences of a human antibody. Humanized antibodies generally have at least three potential advantages for use in human therapy. First, it may interact better with the human immune system, e.g., to destroy target cells more efficiently by complement-dependent cytotoxicity (CDC) or antibody-dependent cellular cytotoxicity (ADCC). Second, the human immune system should not recognize the antibody as foreign. Third, the half-life in the human circulation will be similar to naturally occurring human antibodies, allowing smaller and less frequent doses to be given.

WO93/14220 discloses monoclonal antibodies that bind to the fourth immunoglobulin-like domain of VCAM-1 and bind only to the human VCAM-1. As described above, the monoclonal antibody of the present invention specifically binds to the VCAM-1 expressed in various cells such as the human, mouse and porcine endothelial cells as well as the rat skeletal muscle cells. Moreover, the epitope of the monoclonal antibody of the present invention is different from that of the monoclonal antibody disclosed in WO93/14220.

As the monoclonal antibody of the present invention has a strong affinity to native VCAM-1 expressed in a variety of cell types such as human, mouse, and porcine endothelial cells and rat skeletal muscle cells, it can be used for any application using antigen-recognition to VCAM-1. Furthermore, the monoclonal antibody potently inhibits the binding of leukocytes to activated endothelial cells. Therefore, the invention provides for a method for diagnosing and treating a VCAM-1 related disease.

Accordingly, the monoclonal antibody that specifically binds to both human and mouse VCAM-1 of the present invention may be administered alone or in the form of a pharmaceutical composition for diagnosing and treating VCAM-1 related disease in combination with a conventional carrier.

Moreover, the monoclonal antibody of the present invention may also be used in combination with other antibodies, bioactive agents or materials for various purposes. For example, the present monoclonal antibody may be used in combination with 4B9 or other anti-VCAM-1 antibodies in the treatment of disorders characterized by VCAM-1 expression in endothelium. Alternatively, the present monoclonal antibody may be used in combination with antibodies recognizing other endothelial cell receptors identified in inflammatory events (e.g., ELAM1, ICAM1, etc.) and known drugs treating for inflammatory disease or cancer.

In another embodiment, the present invention relates to a light chain variable region comprising light chain CDR1 as defined by SEQ ID No. 5; light chain CDR2 as defined by SEQ ID No. 6; and light chain CDR3 as defined by SEQ ID No. 7. Preferably, the light chain variable region of the present invention may comprise a light chain of which the amino acid sequence is defined by SEQ ID No. 1 or 13.

In another embodiment, the present invention relates to a heavy chain variable region comprising heavy chain CDR1 as defined by SEQ ID No. 8; heavy chain CDR2 as defined by SEQ ID No. 9 or SEQ ID No. 11; and heavy chain CDR3 as defined by SEQ ID No. 10 or SEQ ID No. 12. Preferably, the heavy chain variable region of the present invention may comprise a heavy chain of which the amino acid sequence is selected from the group consisting of the amino acid sequences that are defined by SEQ ID NOS. 2, 3, 4, 14 and 15.

In another embodiment of the present invention relates to a method for preparing a monoclonal antibody that specifically binds to both human and mouse vascular cell adhesion molecule-1 (VCAM-1). The monoclonal antibody of the present invention can easily be produced by well-known methods for producing a monoclonal antibody. For example, the method can include producing a hybridoma by using B leukocytes obtained from immunized animals (Koeher and Milsteinm, 1976, Nature, 256:495) or using phage display method, and is not limited thereto.

An antibody library using phage display is a method for expressing an antibody on the surface of a phage with genes of the antibody directly obtained from B lymphocytes. Many of the difficulties associated with generating monoclonal antibodies by B-cell immortalization can be overcome by engineering and expressing antibody in *E. coli*, using phage display method.

A conventional phage display comprises:

1) inserting an oligonucleotide having a random sequence into the region corresponding to the N-terminus of a phage coat protein pIII (or pIV); 2) expressing a fusion protein of a natural coat protein and a polypeptide coded by said oligonucleotide having a random sequence; 3) treating a receptor material that can bind to the polypeptide coded by said oligonucleotide; 4) eluting peptide-phage particles bound to the receptors using low pH or a molecule which has binding competitiveness; 5) amplifying the eluted phage by panning in a host cell; 6) repeating the said steps for obtaining desired amounts of phage; and 7) determining a sequence of an active peptide with the DNA sequencing of phage clones selected by panning.

In a preferred embodiment, the present invention relates to a method for preparing the monoclonal antibody of the present invention. Said method can be performed by using phage display techniques, comprising:

(a) immunizing recombinant human VCAM-1/Fc chimera into mammalian animals;
(b) determining antibody titer of the immunized mammalian animals;
(c) purifying polyclonal sera from the immunized mammalian animals;
(d) constructing non-human mammalian animal/human chimeric antibody library; and
(e) selecting anti-VCAM-1 specific antibody from antibody libraries.

A person skilled in the art to which the present invention pertains can perform the above steps easily referring to well-known phage display techniques, which are disclosed in, for example, Barbas et al. (METHODS: A Companion to Methods in Enzymology 2:119, 1991 and J. Virol. 2001, July; 75(14):6692-9) and Winter et al. (Ann. Rev. Immunol. 12:433, 1994).

In detail, (a) the method of immunizing recombinant human VCAM-1/Fc chimera into mammalian animals can be performed by any method known in the art. See, e.g., [Harlow and Lane, Antibodies: A Laboratory Manual, New York: Cold Spring Harbor Press (1990)]. Methods for immunizing non-human animals such as mice, rats, sheep, goats, pings, cattle and horses are well known in the art. In a preferred embodiment, the VCAM/Fc antigen is administered with an adjuvant to stimulate the immune response. Such adjuvants include complete or incomplete Freund's adjuvant, RIBI (muramyl dipeptides) or ISCOM (immunostimulating complexes).

(b) Determining antibody titer of the immunized mammalian animals can be performed by any method known in the art, for example, an enzyme-linked immunoassay (ELISA) or a radioimmunoassay (RIA), preferably an ELISA.

(C) Purifying polyclonal sera from the immunized mammalian animals can be performed by using a variety of well-established isolating and purifying techniques. Such isolating and purifying techniques of polyclonal sera include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

(d) Constructing non-human mammalian animal/human chimeric antibody library; and (e) selecting an anti-VCAM-1 specific antibody from antibody libraries can easily be performed by the above described conventional phage display technique. A phage which can be used for constructing the antibody library may be a filamentous phage, for example, fd, M13, f1, If1, Ike, Zj/Z, Ff, Xf, Pfi and Pf3. Also, a vector, which can be used for the expression of a heterogenous gene on the surface of the filamentous phage, may be a phage vector, for example, fUSE5, fAFF, fd-CAT1 and fdtetDOG; or a phagemid vector, for example, pHEN1, pComb3, pComb8 and pSEX. Preferably, pComb3X phagemid vector may be used. Also, a helper phage, which can be used for providing a natural coat protein required for successful re-infection of recombinant phage, may be, for example, M13KO7 or VSCM13, preferably, VSCM13.

Figure 2:
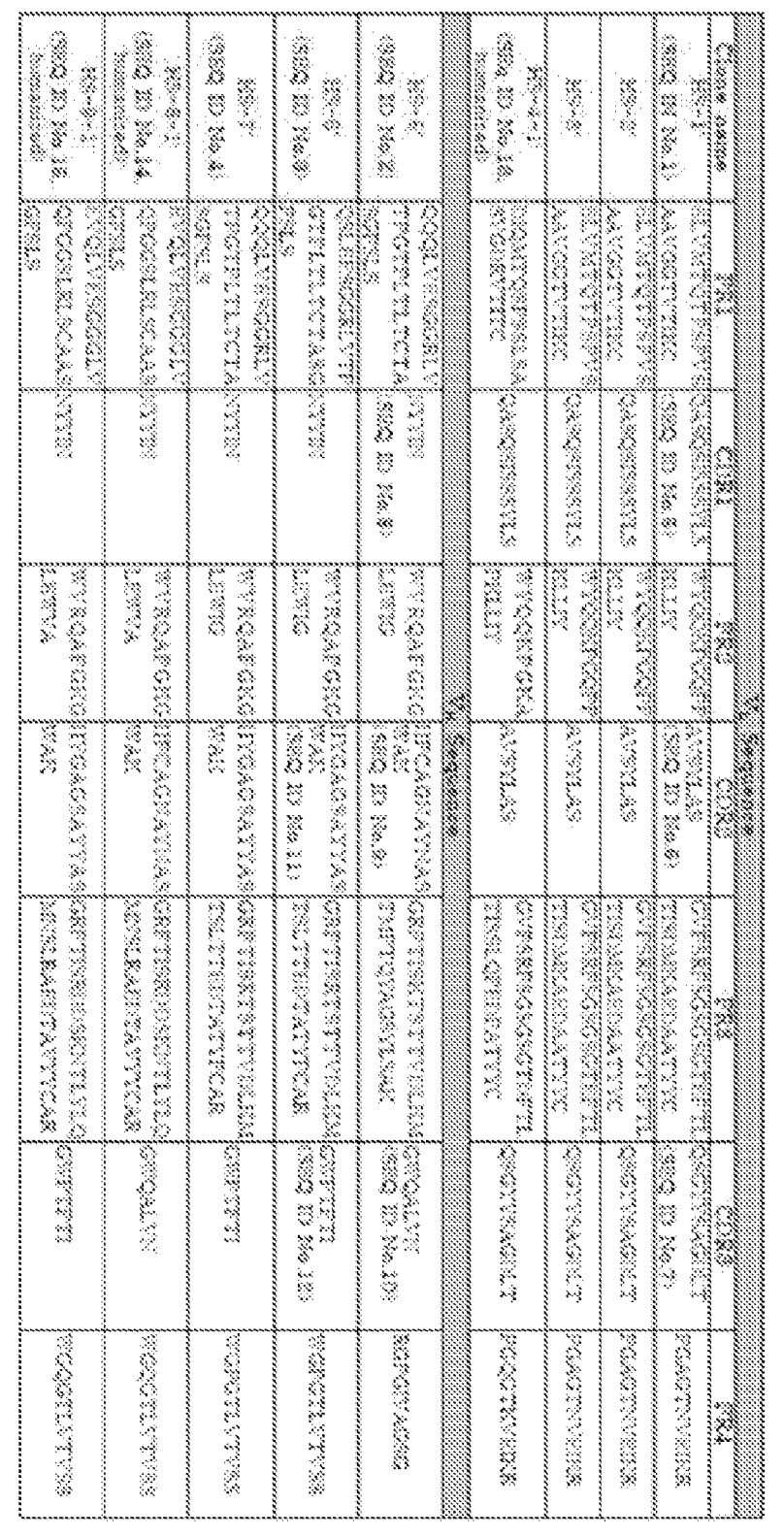

In one preferred example, we first immunized recombinant human VCAM-1/Fc chimera into rabbits to generate recombinant antibody dual-specific to human and mouse VCAM-1. Enzyme immunoassay of rabbit sera collected throughout the immunization courses revealed that all rabbits had elevated antibody titers to the antigen (data not shown). After the fifth booster injection, total RNA was isolated from spleen and bone marrow of the immunized rabbits and subjected to cDNA synthesis. Using three steps of PCR, rabbit/human chimeric antibody library was generated and cloned into phagemid vector pComb3X, yielding a complexity of $5.7 \times 10^9$ independent transformants. After six rounds of biopanning on immobilized mouse VCAM-1, twenty clones were randomly selected, rescued by infection of helper phage, and tested for their reactivity to both human and mouse VCAM-1 in phage enzyme immunoassay. Three of the twenty selected clones showed strong reactivity to both human and mouse VCAM-1. These three individual clones were subsequently analyzed by DNA sequencing. Three clones have quite similar nucleotide sequences and the sequence is shown in FIG. 2.

In order to prevent the immunogenicity of anti-VCAM-1 chimeric Fab in human, we also tried to generate humanized antibody by grafting six complementarity-determining regions (CDRs) of anti-VCAM-1 Fab onto framework in variable regions of known therapeutic humanized antibody. The sequences designed are described in FIG. 2.

Figure 1B:
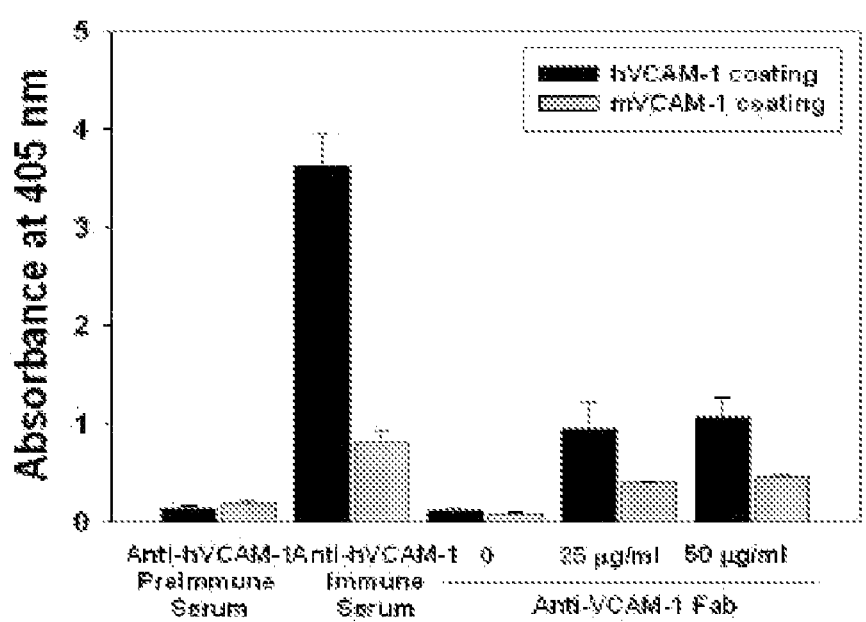
Figure 1C:
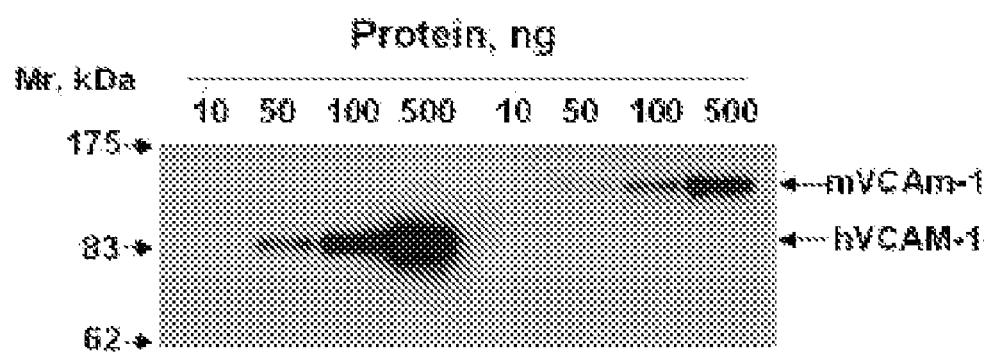

Then, 0.3 mg of anti-VCAM-1 specific Fab was finally obtained from 1 L of a shaking culture that was overexpressed in *E. coli* and purified with an anti-HA affinity column chromatography, followed by characterization of the biochemical and functional properties of the selected VCAM-1 specific Fab. Its purity was confirmed by SDS-PAGE and Coomassie blue staining (FIG. 1A). Enzyme immunoassay experiments revealed that the purified antibody specifically bound to human and mouse VCAM-1. Preimmune sera and immune sera were used for negative and positive control in the experiment set (FIG. 1B). Furthermore, to verify the specificity of the antibody to both human and mouse VCAM-1, purified recombinant human and mouse VCAM-1/Fc chimera were subjected to western blot analysis with the purified Anti-VCAM-1 Fab. The result demonstrated that the purified VCAM-1 Fab successfully reacted to both human and mouse VCAM-1/Fc chimera respectively (FIG. 1C). These findings provided clear evidences that the VCAM-1 Fab has specificity to both human and mouse VCAM-1.

Figure 3:
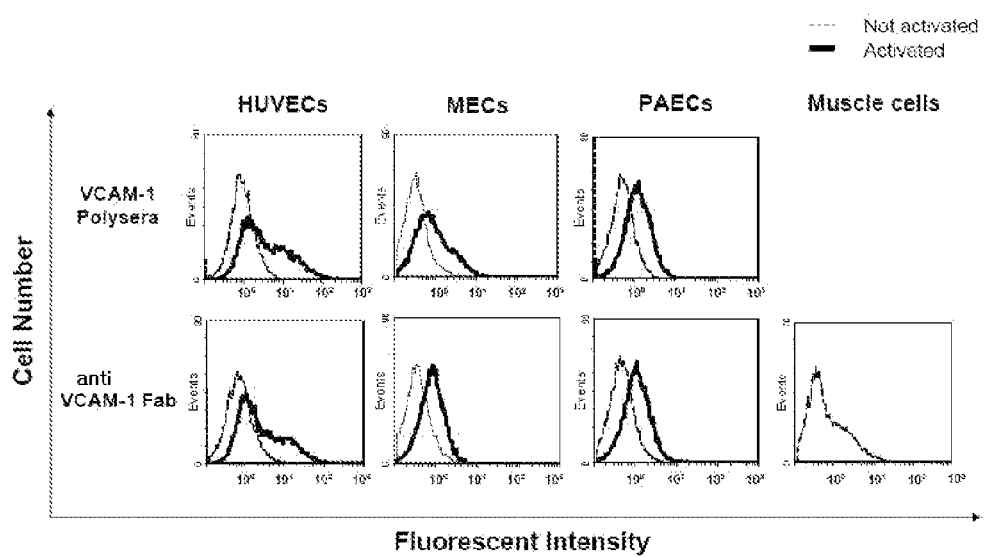
FIG. 3 shows detection of native VCAM-1 expressed in various cell types by anti-VCAM-1 Fab. HUVECs, MECs, PAECs and L6 skeletal muscle cells cultured in the absence (dotted line) or presence (solid line) of hTNFα or $H_2O_2$ as described under Examples were subjected to flow cytometry with anti-VCAM-1 Fab. Purified VCAM-1 specific polysera was used as positive control. The results shown are representative of at least three separate experiments.
Figure 4A:
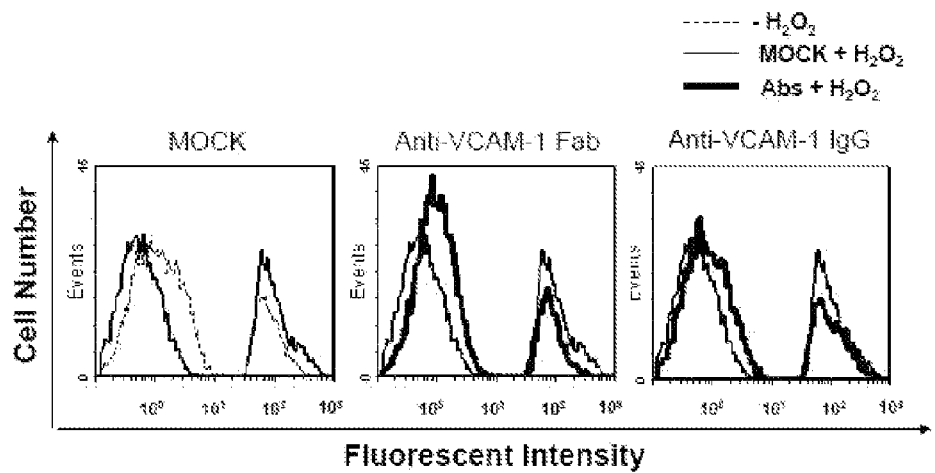
FIGS. 4a and 4b show the neutralizing effect of anti-VCAM-1 Fab on the interaction between leukocytes and endothelial cells.
Figure 4B:
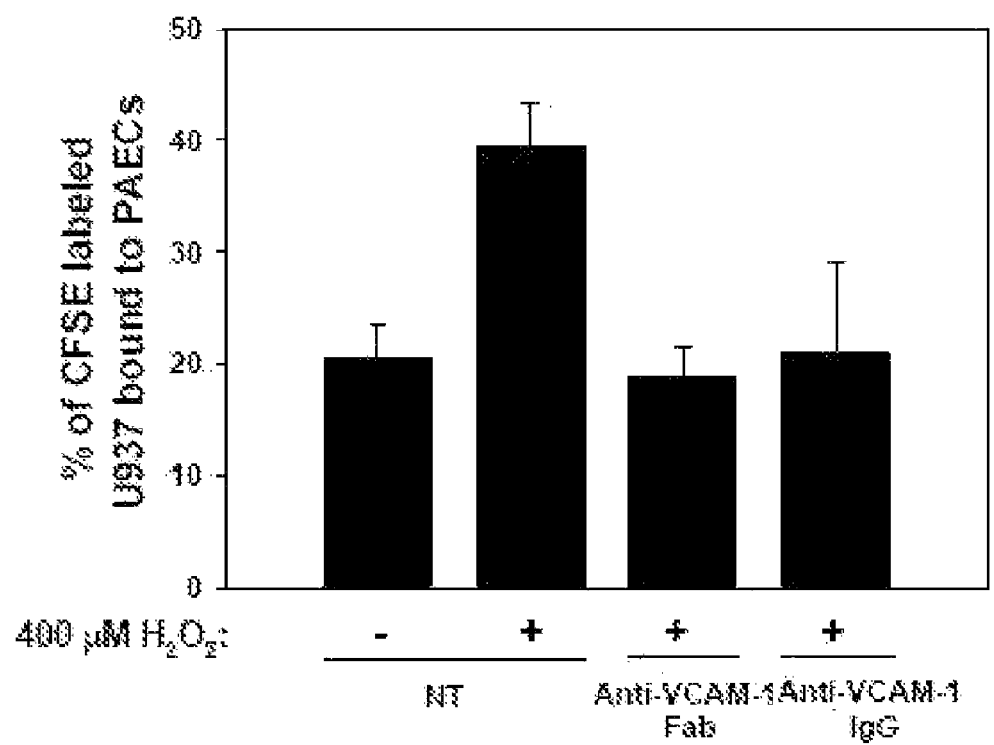

To examine its reactivity toward native VCAM-1, VCAM-1 specific Fab was subsequently analyzed by flow cytometry. The selected Fab was found to bind to VCAM-1 expressed in hTNFα-stimulated HUVECs, $H_2O_2$-activated porcine, and mouse endothelial cells. This Fab was also demonstrated to react to VCAM-1 basally expressed in rat skeletal muscle cells (FIG. 3). Because the interaction between leukocyte and activated endothelial cells is mediated by VCAM-1, we next tested whether the selected Fab could inhibit this interaction. For this purpose, we performed adhesion assay with CFSE-labeled U937 human promonocytic leukocyte and human, mouse, and porcine endothelial cells stimulated with hTNFα or $H_2O_2$ after incubation with the selected Fab. The result obtained revealed a potent inhibition of the interaction between human monocyte and three types of activated endothelial cells (FIG. 4).

In another embodiment, the present invention relates to a composition for diagnosing a disease related to the expression of VCAM-1 or a VCAM-1 mediated disease, wherein the composition comprises the monoclonal antibody that specifically binds to both human and mouse vascular cell adhesion molecule-1 and to a method for diagnosing said disease using the same.

For example, VCAM-1 may be detected by reacting a monoclonal antibody of the present invention with a biological sample and detecting formation of an antigen-antibody complex.

The "biological sample" as used herein, may be a tissue, a cell, whole blood, serum, plasmic fluid, autoptical sample of tissue (brain, skin, lymph node, spinal cord), supernatant of cell culture, disruptive eukaryotic cell and bacterial expression system, which is not limited herein. Existence of VCAM-1, inflammatory disease or cancer can be detected by reacting manipulated or non-manipulated biological sample with the monoclonal antibody of the present invention.

The "antigen-antibody complex" as used herein, refers to a combination material of VCAM-1 antigen in the sample and the monoclonal antibody of the present invention. Formation of such antigen-antibody complex may be detected by a method selected from a group consisting of colormetric method, electrochemical method, fluorimetric method, luminometry, particle counting method, visual assessment and scintillation counting method. However, the method is not limited to the above examples and has a variety of applications.

Various labels may be used for detecting an antigen-antibody complex in the present invention. Non-limiting examples of the label enabling quantitative or qualitative measurement of the formation of antigen-antibody complexes include enzymes, fluorescent substances, ligands, luminescent substances, microparticles, redox molecules and radioactive isotopes.

Suitable examples of materials that can be used as a label, include acetylcholine esterase, alkaline phosphatase, β-D-galctosidase, horseradish peroxidase and β-lactamase as an enzyme; fluorescein, $Eu^{3+}$, $Eu^{3+}$ chelate and cryptate as a fluorescent; biotin-derivatives as a ligand; acridinium ester, isoluminol derivatives as a luminescent; colloidal gold, colored latex as a microparticle; and $^{57}Co$, $^{3}H$, $^{125}I$, $^{125}I$-Bonton Hunter reagent as a radioactive isotopes.

Preferably, the antigen-antibody complex may be detected by using ELISA. ELISA techniques include a direct ELISA using a labeled antibody which recognizes an antigen adhered to a support body; an indirect ELISA using a labeled secondary antibody which recognizes a captured antibody of an antigen-antibody complex wherein the antigen adhered to a support body; a direct sandwich ELISA using another labeled antibody which recognizes an antigen of an antigen-antibody complex; and an indirect sandwich ELISA using another labeled secondary antibody which recognizes a captured antibody of an antigen-antibody complex. The monoclonal antibody may have a detectable label, otherwise the antigen-antibody complex may be detected by treating another antibody which can capture the monoclonal antibody of the present invention and has a detectable label.

In another embodiment, the present invention relates to a composition for treating a disease related to the expression of VCAM-1 or a VCAM-1 mediated disease, wherein a composition comprises the monoclonal antibody that specifically binds to both human and mouse vascular cell adhesion molecule-1 and a pharmaceutically accepted carrier or a excipient, and to a method for treating said disease using the same. Preferably, the disease is an inflammatory disease or a cancer.

The present composition may be administered in a single or multiple dosage in an amount sufficient for treating the disease. The composition of the present invention may be administered in a non-limiting form of solutions, powders, aerosols, capsules, enteric-coated tablets or capsules or suppositories. A variety of modes of administration are contemplated, including intraperitoneally, intravenously, intramuscularly, subcutaneously, intradermally, orally, topically, intranasally, intrapulmonarily and intrarectally, but the present invention is not limited to these exemplified modes of administration. However, since peptides are digested upon oral administration, active ingredients of a composition for oral administration should be coated or formulated for protection against degradation in the stomach. In addition, the pharmaceutical composition of the present invention may be administered using a certain apparatus capable of transporting the active ingredients into a target cell.

The present composition may be administered in a pharmaceutically effective amount sufficient for treating the disease. The "a pharmaceutically effective amount" refers to an amount sufficient for preventing and/or treating disease in a reasonable ratio of advantage/risk, which can be applicable to medical treatment or prevention.

The effective dosage level may vary according to a variety of factors, including properties and severity of the illness, drug activity, the patient's age, weight, health, gender and drug sensitivity, administration time of the composition of the present invention, administration modes and routes, excretion ratio of the composition, period of treatment, drug in combination with the composition of the present invention or administered simultaneously and the other factors, and may be readily determined by specialists in the art. The present composition may be administered either simultaneously or sequentially with pharmaceutical or physiological ingredients, and may also be administered in combination with conventional therapeutic agents in a sequential or simultaneous manner.

In case of administrating the composition of the present invention in a pharmaceutically effective amount, the monoclonal antibody of the present invention, which has strong affinity to VCAM-1, specifically binds to VCAM-1 expressed on an endothelial cell and results in neutralization of VCAM-1. Ultimately, the monoclonal antibody of the present invention inhibits the adhesion of a leukocyte to the endothelial cell and treats VCAM-1 mediated disease. Preferably, VCAM-1 mediated disease is an inflammatory disease or a cancer, and more preferably, the inflammatory disease is selected from the group consisting of arthritis, multiple sclerosis, bowl disease, asthma, atherosclerosis, myocardial infarction, transplantation rejection and stroke.

All of the references cited herein are incorporated by reference in their entirety. Also, those skilled in the art will recognize, or be able to ascertain using no more than routine experimentation, many equivalents to the specific embodiments of the invention specifically described herein. Such equivalents are intended to be encompassed in the scope of the claims.

A better understanding of the present invention may be obtained through the following examples which are set forth to illustrate, but are not to be construed as the limit of the present invention.

EXAMPLES

1. Materials

Recombinant human and mouse VCAM-1/Fc chimeras were purchased from R&D Systems (Minneapolis, Minn.). The Expand High Fidelity PCR System and HRP-conjugated anti-influenza A virus hemagglutinin (HA) antibody (3F10) were from Roche (Mannheim, Germany). TMB solution was from Pierce (Rockford, Ill.). 5,6-carboxy-fluorescein succinimidyl ester (CSFE) and fluorescein isothiocyanate (FITC)-labeled goat anti-rabbit secondary antibody, were obtained from Molecular Probes. Enhanced chemiluminescence and HRP-conjugated anti-rabbit IgG antibody were purchased from Amersham Biosciences (Uppsala, Sweden). Aprotinin, leupeptin, paraformaldehyde, human TNFα (hTNFα), and hydrogen peroxide were from Sigma.

Human umbilical vein endothelial cells (HUVECS) and EGM-2 bullet kit were from Cambrex. Goat anti-human Fab polyclonal antibodies were from Bethyl Laboratories (Montgomery, Tex.). Penicillin/streptomycin, fetal bovine serum, RPMI, Superscript Preamplification System and Dulbecco's modified Eagle's minimal essential medium were purchased from Life Technologies (Gaithersburg, Md.). Porcine aortic endothelial cell lines (PAECs) were kindly provided from Dr. Curie Ahn (Seoul National University, Seoul, South Korea). SV40 transformed mouse endothelial pancreatic islet cell line MS-1 (MILE SEVEN1) was from Dr. Pann-Ghill Suh (POSTECH, Pohang, South Korea). L6 rat skeletal muscle cells were from Dr. Sang Chul Park (Seoul National University, Seoul, South Korea).

2. Cell Culture

The PAECs, MECs and L6 muscle cells were maintained in Dulbecco's modified Eagle's medium supplemented with 10% (v/v) fetal bovine serum and 1% (v/v) penicillin/streptomycin respectively. HUVECs were maintained in EGM-2 followed by manufacturer's instruction. U937 human promonocytic leukocyte cell lines were cultured in RPMI supplemented with 10% (v/v) fetal bovine serum and 1% (v/v) penicillin/streptomycin. All cells were cultured at 37° C. in a humidified $CO_2$-controlled (5%) incubator.

3. Immunization of Human VCAM-1/Fc Chimera 2.5 μg of recombinant human VCAM-1/Fc chimera was mixed in 2 ml of PBS, emulsified with MPL+TDM+CWS adjuvant pre-incubated at 37° C. for 30 min and then injected into New Zealand white rabbits. The antibody titer of immunized rabbits was determined by enzyme linked immunosorbent assay (ELISA) using HRP-conjugated anti-rabbit IgG antibodies as secondary antibodies. After five booster injections on a 3-week inter-injection interval, polyclonal sera from immunized rabbit were purified with protein A sepharose bead.

4. Construction of Rabbit/Human Chimeric Antibody Library

The protocol is followed with a minor modification by Barbas et al., 2001. In brief, first-strand cDNA was synthesized from total RNA of spleen and bone marrow from recombinant human VCAM-1/Fc chimera-immunized rabbits using the SUPERSCRIPT Preamplification System with oligo(dT) priming. To construct VCAM-1 Fab library, PCR was performed with three steps of PCR. With the first round PCR, rabbit $V_L$ and $V_H$ were amplified from rabbit cDNA and human $C_L$ and $C_{H1}$ from a pComb3X expression vector containing a human Fab. Then, with the second round PCR, rabbit/human chimeric light chain and heavy chain were generated by combining rabbit $V_L$ with human $C_K$ and rabbit $V_H$ and with human $C_{H1}$ respectively using overlap extension PCR. In the third round of PCR, the chimeric light chain products and heavy chain products were joined by overlap extension PCR. The resulting Fab encoding library was digested with Sfi I (Roche, Indianapolis, Ind.), ligated into phagemid vector pComb3X, and transformed into *E. coli* strain ER2738 cells (New England Biolabs) cultured in SB medium containing 10 μg/ml of tetracycline. The cultures were then incubated for 1 hr in a 37° C. shaker after the addition of 30 μg/ml of carbenicillin. VCSM13 helper phage ($>1 \times 10^{12}$ pfu/ml) and 70 μg/ml of kanamycin were added to the cultures and incubated overnight at 37° C. Following centrifugation at 5,000 rpm for 15 min, the collected supernatant was incubated with 8 g of polyethylene glycol-8000 (PEG-8000) and 6 g of NaCl on ice for 30 min and then centrifuged at 9,000 rpm for 20 min. The phage pellet was resuspended in Tris-buffered saline (TBS) containing 3% (w/v) BSA and 0.02% $NaN_3$.

5. Selections of Anti-VCAM-1 Specific Antibody from Antibody Libraries

A total of six rounds of panning were performed. After coating of 2.5 μg of recombinant mouse VCAM-1/Fc chimera overnight at 4° C. in a microtiter plate, TBS containing 5% (w/v) BSA was incubated for blocking nonspecific binding for 2 hrs at 37° C. and then 50 µl of recombinant phages in TBS containing 3% (v/v) BSA was incubated for 2 hrs at 37° C. Nonspecific phages were removed by washing with TBS containing 0.1% (v/v) Tween 20. Binding phages were eluted with 0.1 M Glycine/HCl, pH 2.2 and neutralized with 1 M Tris-HCl, pH 9.1. The eluate was used to transfect logarithmically growing ER2738 and the ER2738 harboring the phagemid library was grown by rescue of phagemid with helper phage VCSM13 for overnight amplification. Phage preparations were purified and concentrated by the addition of PEG and NaCl as described above. This overall selection procedure was repeated 6 times and the washing steps were increased from 1 time in the first round to 3 times in the second, third, and fourth round, 6 times in the fifth round, and 10 times in the sixth round.

6. Overexpression and Purification of Anti-VCAM-1 Fab 0.5 µg of phagemid DNA was transformed into HB2151 *E. coli* and the cells were grown in LB medium containing 50 mg/ml carbenicillin with constant shaking at 37° C. When the optical density at 600 nm reached 0.6, the cells were grown overnight at 30° C. After centrifugation at 15,000×g for 30 min, the collected supernatants were concentrated with Labscale TFF System (Milipore, Bedford, Mass.) and then incubated with anti-hemagglutin (HA) antibody conjugated protein A Sepharose. After washing with buffer containing 50 mM sodium, pH 8.2, the Fab was eluted with 0.1 M glycine, pH 2.2 and the fraction was immediately neutralized with 1 M Tris, pH 9.2 to adjust physiological pH. After dialysis in PBS overnight at 4° C., the concentration of the samples was calculated by measuring the optical density at 280 nm. The purity of the Fab was detected with Coomassie Brilliant staining.

7. Immunoblot Analysis

After assaying with Bradford solution, proteins were denatured by boiling for 5 min at 95° C. in a Laemmli sample buffer, separated by SDS PAGE, and transferred to nitrocellulose membranes by electroblotting using the wet transfer system (Amersham Biosciences). After blocking in TTBS buffer (10 mM Tris/HCl, pH 7.5, 150 mM NaCl, and 0.05% Tween 20) containing 5% (w/v) skim milk powder, the membranes were incubated with individual monoclonal or polyclonal antibodies, which was subsequently followed by another incubation with anti-mouse or anti-rabbit immunoglobulin G, as required, coupled with horseradish peroxidase. Detection was performed using an enhanced chemiluminescence kit according to manufacturer instructions. To reprobe with another first antibody, membranes were incubated in striping buffer (62.5 mM Tris-HCl, pH 6.0, 100 mM 2-mercaptoethanol [2-ME], and 2% SDS) for 30 minutes at 50° C., washed, and then used for further study.

8. Enzyme-Linked Immunosorbent Assay (ELISA)

Recombinant human and mouse VCAM-1/Fc chimera dissolved in PBS, at a concentration of 2 µg/ml, were incubated respectively in the wells of a microtiter plate overnight at 4° C. After brief washing with PBS, the plate was blocked with 3% (w/v) BSA in PBS, incubated with the polysera (1:2000) for 1 hr at 37° C., and washed more than three times with PBS containing 0.05% Tween 20. The amount of Fab bound to the plate was detected by the application of horse radish peroxidase conjugated anti-HA mAb 3F10 (Roche). Optical density was measured at 405 nm by a microtiter plate reader (Labsystems, Barcelona, Spain) after incubation with ABTS substrate solution (2,2'-Azino-bis-13-ethylbenzthiazoline-6-sulfonic acid, MP Biomedicals, Inc) solution for 30 min at 37° C. For competition ELISA, VCAM-1 peptides were incubated in a microtiter plate for 1 hr at 37° C. after antigen coating. The next procedures were similar as described above.

9. Treatment of $H_2O_2$ and hTNFα in Human, Mouse, and Porcine Endothelial Cells For PAECs and MECs, 400 µM of $H_2O_2$ was treated for 24 hrs for detecting maximal expression of VCAM-1 in the cells. For HUVECs, 20 ng/ml of hTNFα was treated for 24 hrs.

10. Flow Cytometry

All cells were plated at a density of $3 \times 10^5$ cells/well in 60-mm dishes and treated with $H_2O_2$ or hTNFα respectively and then the cells were trypsinized. After brief centrifugation at 1,500 rpm for 5 min, the pellets were washed with 1×PBS and blocking buffer containing 1% (w/v) BSA in 1×PBS and 50 µl of anti-VCAM-1 specific Fab in blocking buffer adjusted to 50 µg/ml of final concentration was incubated with the cells at 37° C. for 50 min. After centrifugation at 2000 rpm for 5 min, the cells were washed with 140 µl of blocking buffer and or FITC-labeled anti-human Fab antibody (1:100) was incubated at 37° C. for 30 min. Following brief centrifugation, the pellets were washed with 140 µl of blocking buffer and then the final pellets were resuspended with 300 µl of 2% (w/v) paraformaldehyde in PBS. The VCAM-1 expression was analyzed by a flow cytometer (Beckmann Coulter, Calif., USA).

11. CFSE Labeling

After harvesting U937 cell, the cells were washed two times with HBSS. The washed cells ($1 \times 10^7$ cells) were incubated with CFSE solution in DMSO to adjust final concentration to 2.5 µM CFSE on ice in the dark for 5 min. For quenching the labeling process, 1/10 volume of fetal bovine serum was added and gently mixed for 1 min. After the brief centrifugation, the cells were resuspended and counted before use.

12. Cell Adhesion and Neutralization Assay

Leukocyte adhesion assays were performed with minor modification. Briefly, $3 \times 10^5$ cells of endothelial cells plated on 60 mm dishes were stimulated with $H_2O_2$ or hTNFα as indicated and then the cells were washed one time with 1×PBS. Following CFSE labeling with U937 promonocytic leukocytes, the labeled cells as indicated were incubated with $H_2O_2$ or hTNFα stimulated endothelial cells for 1 hr at 37° C. and then unbounded cells were washed 5 times with 1×PBS containing 0.2 mM $CaCl_2$ and 0.1 mM $MgCl_2$. The final cells were trypsinized and then subjected to FACS analysis. For neutralizing assay, endothelial cells stimulated with $H_2O_2$ or hTNFα for 1 day were incubated with anti-VCAM-1 polyclonal antibodies or anti-VCAM-1 Fab as indicated for 1 hr at 37° C. before the addition of CFSE labeled U937. Following procedures are the same to above procedures.

INDUSTRIAL APPLICABILITY

The monoclonal antibody of the present invention is the first recombinant monoclonal antibodies that is specific to human and mouse VCAM-1. In addition, the monoclonal antibody of the present invention shows a strong affinity to VCAM-1 expressed in rat skeletal muscle and porcine endothelial cells as well as human and mouse endothelial cells and is found to strongly inhibit the interaction between leukocytes and activated endothelial cells. To our knowledge, this is the first recombinant monoclonal antibodies that is specific to human and mouse VCAM-1 and can potently inhibit VCAM-1 mediated leukocyte adhesion to endothelial cells. Accordingly, the monoclonal antibody of the present invention can inhibit a VCAM-1 mediated adhesion of leukocytes to endothelial cells and potently treat VCAM-1 mediated disease, especially inflammatory disease or cancer.

What is claimed is:

1. A monoclonal antibody that specifically binds to both human and mouse vascular cell adhesion molecule-1 (VCAM-1), comprising:
   (a) a light chain CDR 1 region defined by SEQ ID NO:5, a light chain CDR 2 region defined by SEQ ID NO:6, and a light chain CDR 3 region defined by SEQ ID NO:7; and
   (b) a heavy chain CDR 1 region defined by SEQ ID NO:8, a heavy chain CDR 2 region defined by SEQ ID NO: 9 or 11, and a heavy chain CDR 3 region defined by SEQ ID NO: 10 or 12.

2. The monoclonal antibody according to claim 1 further specifically binding to human, mouse, rat, and porcine VCAM-1.

3. The monoclonal antibody according to claim 2, wherein the VCAM-1 is expressed in endothelial cells, or skeletal muscle cells.

4. The monoclonal antibody according to claim 1, which inhibits the interaction between leukocytes and activated endothelial cells.

5. The monoclonal antibody according to claim 1, wherein the monoclonal antibody is a recombinant monoclonal antibody.

6. The monoclonal antibody according to claim 1, wherein
   (1) The heavy chain CDR 2 region is defined by SEQ ID NO: 9, and the heavy chain CDR 3 region is defined by SEQ ID NO: 10; or
   (2) The heavy chain CDR 2 region is defined by SEQ ID NO: 11, and the heavy chain CDR 3 region is defined by SEQ ID NO: 12.

7. The monoclonal antibody according to claim 5, wherein the monoclonal antibody is humanized.

8. A method of preparing the antibody according to claim 1 comprising:
   (i) immunizing recombinant human VCAM-1/Fc chimera into mammalian animals;
   (ii) constructing non-human mammalian animal/human chimeric antibody library; and
   (iii) selecting anti-VCAM-1 specific antibody from antibody libraries.

9. A method for detecting VCAM-1 expressing cells comprising contacting a sample with the monoclonal antibody according to claim 1.

10. A method for inhibiting VCAM-1 mediated adhesion of a leukocyte to endothelial cell comprising contacting the endothelial cell with the monoclonal antibody according to claim 1 in vitro.

11. A composition comprising the monoclonal antibody according to claim 1 and an effective carrier thereof.

12. A composition comprising the monoclonal antibody according to claim 1 and a pharmaceutically effective carrier thereof.

13. The monoclonal antibody according to claim 1, wherein the light chain amino acid sequence is defined by SEQ ID NO:1.

14. The monoclonal antibody according to claim 7, wherein the light chain of which the amino acid sequence is defined by SEQ ID NO:13.

15. The monoclonal antibody according to claim 1, wherein the heavy chain amino acid sequence is defined by SEQ ID NOs: 2, 3, or 4.

16. The monoclonal antibody according to claim 7, comprising wherein the heavy chain amino acid sequence is defined by SEQ ID NOs: 14 or 15.

* * * * *

SEQUENCE LISTING

```
<160> NUMBER OF SEQ ID NOS: 15

<210> SEQ ID NO 1
<211> LENGTH: 111
<212> TYPE: PRT
<213> ORGANISM: Artificial Sequence
<220> FEATURE:
<223> OTHER INFORMATION: a light chain variable region

<400> SEQUENCE: 1

Glu Leu Val Met Thr Gln Thr Pro Ser Pro Val Ser Ala Ala Val Gly
  1               5                  10                  15

Gly Thr Val Thr Ile Lys Cys Gln Ala Ser Gln Ser Ile Ser Ser Ser
             20                  25                  30

Tyr Leu Ser Trp Tyr Gln Gln Lys Pro Gly Gln Pro Pro Lys Leu Leu
         35                  40                  45

Ile Tyr Ala Val Ser Tyr Leu Ala Ser Gly Val Pro Ser Arg Phe Ser
     50                  55                  60

Gly Ser Gly Ser Gly Thr Glu Phe Thr Leu Thr Ile Ser Asp Met Lys
 65                  70                  75                  80

Ala Glu Asp Ala Ala Thr Tyr Tyr Cys Gln Ser Gly Tyr Tyr Ser Ala
                 85                  90                  95

Gly Asp Leu Thr Phe Gly Ala Gly Thr Asn Val Glu Ile Lys Arg
            100                 105                 110

<210> SEQ ID NO 2
<211> LENGTH: 111
<212> TYPE: PRT
<213> ORGANISM: Artificial Sequence
<220> FEATURE:
<223> OTHER INFORMATION: a heavy chain variable region

<400> SEQUENCE: 2

Gln Gln Gln Leu Val Glu Ser Gly Gly Arg Leu Val Thr Pro Gly Thr
  1               5                  10                  15

Pro Leu Thr Leu Thr Cys Thr Ala Ser Gly Phe Ser Leu Ser Asn Tyr
             20                  25                  30

Tyr Ile Asn Trp Val Arg Gln Ala Pro Gly Lys Gly Leu Glu Trp Ile
         35                  40                  45

Gly Ile Ile Phe Cys Ala Gly Asn Ala Tyr Asn Ala Ser Trp Ala Lys
     50                  55                  60

Gly Arg Phe Thr Ile Ser Lys Thr Ser Thr Val Asp Leu Lys Met
 65                  70                  75                  80

Thr Met Pro Thr Gln Tyr Ala Gly Ser Tyr Leu Ser Ala Lys Gly Trp
                 85                  90                  95

Gln Ala Leu Val Asn Arg Gly Pro Gly Ile Val Ala Gly Ser Gly
            100                 105                 110

<210> SEQ ID NO 3
<211> LENGTH: 112
<212> TYPE: PRT
<213> ORGANISM: Artificial Sequence
```

```
<220> FEATURE:
<223> OTHER INFORMATION: a heavy chain variable region

<400> SEQUENCE: 3

Gln Ser Leu Glu Glu Ser Gly Gly Arg Leu Val Thr Pro Gly Thr Pro
 1               5                  10                  15

Leu Thr Leu Thr Cys Thr Ala Ser Gly Phe Ser Leu Ser Asn Tyr Tyr
            20                  25                  30

Ile Asn Trp Val Arg Gln Ala Pro Gly Lys Gly Leu Glu Trp Ile Gly
        35                  40                  45

Ile Ile Tyr Gly Ala Gly Ser Ala Tyr Tyr Ala Ser Trp Ala Lys Gly
    50                  55                  60

Arg Phe Thr Ile Ser Arg Thr Ser Thr Thr Val Asp Leu Lys Met Thr
65                  70                  75                  80

Ser Leu Thr Thr Glu Asp Thr Ala Thr Tyr Phe Cys Ala Arg Gly Trp
                85                  90                  95

Pro Thr Phe Thr Ile Trp Gly Pro Gly Thr Leu Val Thr Val Ser Ser
            100                 105                 110

<210> SEQ ID NO 4
<211> LENGTH: 113
<212> TYPE: PRT
<213> ORGANISM: Artificial Sequence
<220> FEATURE:
<223> OTHER INFORMATION: a heavy chain variable region

<400> SEQUENCE: 4

Gln Gln Gln Leu Val Glu Ser Gly Gly Arg Leu Val Thr Pro Gly Thr
 1               5                  10                  15

Pro Leu Thr Leu Thr Cys Thr Ala Ser Gly Phe Ser Leu Ser Asn Tyr
            20                  25                  30

Tyr Ile Asn Trp Val Arg Gln Ala Pro Gly Lys Gly Leu Glu Trp Ile
        35                  40                  45

Gly Ile Ile Tyr Gly Ala Gly Ser Ala Tyr Tyr Ala Ser Trp Ala Lys
    50                  55                  60

Gly Arg Phe Thr Ile Ser Arg Thr Ser Thr Thr Val Asp Leu Lys Met
65                  70                  75                  80

Thr Ser Leu Thr Thr Glu Asp Thr Ala Thr Tyr Phe Cys Ala Arg Gly
                85                  90                  95

Trp Pro Thr Phe Thr Ile Trp Gly Pro Gly Thr Leu Val Thr Val Ser
            100                 105                 110

Ser

<210> SEQ ID NO 5
<211> LENGTH: 12
<212> TYPE: PRT
<213> ORGANISM: Artificial Sequence
<220> FEATURE:
<223> OTHER INFORMATION: CDR1 of a light chain variable region

<400> SEQUENCE: 5

Gln Ala Ser Gln Ser Ile Ser Ser Ser Tyr Leu Ser
 1               5                  10

<210> SEQ ID NO 6
<211> LENGTH: 7
<212> TYPE: PRT
<213> ORGANISM: Artificial Sequence
<220> FEATURE:
<223> OTHER INFORMATION: CDR2 of a light chain variable region
```

```
<400> SEQUENCE: 6

Ala Val Ser Tyr Leu Ala Ser
 1               5

<210> SEQ ID NO 7
<211> LENGTH: 11
<212> TYPE: PRT
<213> ORGANISM: Artificial Sequence
<220> FEATURE:
<223> OTHER INFORMATION: CDR3 of a light chain variable region

<400> SEQUENCE: 7

Gln Ser Gly Tyr Tyr Ser Ala Gly Asp Leu Thr
 1               5                  10

<210> SEQ ID NO 8
<211> LENGTH: 5
<212> TYPE: PRT
<213> ORGANISM: Artificial Sequence
<220> FEATURE:
<223> OTHER INFORMATION: CDR1 of a heavy chain variable region

<400> SEQUENCE: 8

Asn Tyr Tyr Ile Asn
 1               5

<210> SEQ ID NO 9
<211> LENGTH: 15
<212> TYPE: PRT
<213> ORGANISM: Artificial Sequence
<220> FEATURE:
<223> OTHER INFORMATION: CDR2 of a heavy chain variable region

<400> SEQUENCE: 9

Ile Ile Phe Cys Ala Gly Asn Ala Tyr Asn Ala Ser Trp Ala Lys
 1               5                  10                  15

<210> SEQ ID NO 10
<211> LENGTH: 7
<212> TYPE: PRT
<213> ORGANISM: Artificial Sequence
<220> FEATURE:
<223> OTHER INFORMATION: CDR3 of a heavy chain variable region

<400> SEQUENCE: 10

Gly Trp Gln Ala Leu Val Asn
 1               5

<210> SEQ ID NO 11
<211> LENGTH: 15
<212> TYPE: PRT
<213> ORGANISM: Artificial Sequence
<220> FEATURE:
<223> OTHER INFORMATION: CDR2 of a heavy chain variable region

<400> SEQUENCE: 11

Ile Ile Tyr Gly Ala Gly Ser Ala Tyr Tyr Ala Ser Trp Ala Lys
 1               5                  10                  15

<210> SEQ ID NO 12
<211> LENGTH: 7
<212> TYPE: PRT
<213> ORGANISM: Artificial Sequence
<220> FEATURE:
<223> OTHER INFORMATION: CDR3 of a heavy chain variable region
```

```
<400> SEQUENCE: 12

Gly Trp Pro Thr Phe Thr Ile
 1               5

<210> SEQ ID NO 13
<211> LENGTH: 111
<212> TYPE: PRT
<213> ORGANISM: Artificial Sequence
<220> FEATURE:
<223> OTHER INFORMATION: a humanized light chain variable region

<400> SEQUENCE: 13

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Ser Ile Ser Ser Ser
                20                  25                  30

Tyr Leu Ser Trp Tyr Gln Gln Lys Pro Gly Lys Ala Pro Lys Leu Leu
            35                  40                  45

Ile Tyr Ala Val Ser Tyr Leu Ala Ser Gly Val Pro Ser Arg Phe Ser
        50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Ser Gly Tyr Tyr Ser Ala
                85                  90                  95

Gly Asp Leu Thr Phe Gly Gln Gly Thr Lys Val Glu Ile Lys Arg
            100                 105                 110

<210> SEQ ID NO 14
<211> LENGTH: 115
<212> TYPE: PRT
<213> ORGANISM: Artificial Sequence
<220> FEATURE:
<223> OTHER INFORMATION: a humanized heavy chain variable region

<400> SEQUENCE: 14

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Ser Asn Tyr
                20                  25                  30

Tyr Ile Asn Trp Val Arg Gln Ala Pro Gly Lys Gly Leu Glu Trp Val
            35                  40                  45

Ala Ile Ile Phe Cys Ala Gly Asn Ala Tyr Asn Ala Ser Trp Ala Lys
        50                  55                  60

Gly Arg Phe Thr Ile Ser Arg Asp Asp Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg Gly Trp Gln Ala Leu Val Asn Trp Gly Gln Gly Thr Leu Val Thr
            100                 105                 110

Val Ser Ser
        115

<210> SEQ ID NO 15
<211> LENGTH: 115
<212> TYPE: PRT
<213> ORGANISM: Artificial Sequence
<220> FEATURE:
<223> OTHER INFORMATION: a humanized heavy chain variable region

<400> SEQUENCE: 15
```

-continued

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Ser Asn Tyr
            20                  25                  30

Tyr Ile Asn Trp Val Arg Gln Ala Pro Gly Lys Gly Leu Glu Trp Val
        35                  40                  45

Ala Ile Ile Tyr Gly Ala Gly Ser Ala Tyr Tyr Ala Ser Trp Ala Lys
    50                  55                  60

Gly Arg Phe Thr Ile Ser Arg Asp Asp Ser Lys Asn Thr Leu Tyr Leu
65              70                  75                  80

Gln Met Asn Ser Leu Arg Ala Glu Asp Thr Ala Val Tyr Tyr Cys Ala
                85                  90                  95

Arg Gly Trp Pro Thr Phe Thr Ile Trp Gly Gln Gly Thr Leu Val Thr
            100                 105                 110

Val Ser Ser
        115
```